United States Patent [19]
Moore et al.

[11] Patent Number: 4,750,495
[45] Date of Patent: Jun. 14, 1988

[54] OXYGEN SENSING PACEMAKER

[75] Inventors: Alan A. Moore, Blaine; Dennis A. Brumwell, Bloomington, both of Minn.

[73] Assignee: Medtronic, Inc., Minneapolis, Minn.

[21] Appl. No.: 58,300

[22] Filed: Jun. 5, 1987

[51] Int. Cl.$^4$ ............................................. A61N 1/36
[52] U.S. Cl. ........................... 128/419 PG; 128/633; 128/664; 128/665
[58] Field of Search ................ 128/419 PG, 633, 634, 128/664, 665, 666, 667

[56] References Cited

U.S. PATENT DOCUMENTS

| | | | |
|---|---|---|---|
| 3,349,762 | 10/1967 | Kapany | 128/666 |
| 3,648,707 | 3/1972 | Greatbatch | 128/419 P |
| 4,059,116 | 11/1977 | Adams | 128/419 PG |
| 4,202,339 | 5/1980 | Wirtzfeld et al. | 128/419 PG |
| 4,344,437 | 8/1982 | Markowitz | 128/419 PG |
| 4,374,382 | 2/1983 | Markowitz | 340/870.01 |
| 4,399,820 | 8/1983 | Wirtzfeld et al. | 128/419 PG |
| 4,428,378 | 1/1984 | Anderson et al. | 128/419 PG |
| 4,467,807 | 8/1984 | Bornzin | 128/419 PG |
| 4,523,279 | 6/1985 | Sperinde et al. | 128/666 |
| 4,556,063 | 12/1985 | Thompson et al. | 128/419 PT |

OTHER PUBLICATIONS

Brochure entitled "Enertrax TM Model 7100 Atrial Synchronous Ventricular Inhibited Pacemaker" published by Medtronic, Inc., Jul. 1982, pp. 1-31.

Primary Examiner—William E. Kamm
Attorney, Agent, or Firm—Reed A. Duthler; Joseph F. Breimayer; John L. Rooney

[57] ABSTRACT

A demand pacemaker which regulates its pacing rate based upon sensed oxygen saturation percentage. The pacemaker employs a two wavelength reflectance oximeter as a sensor. The sensor includes an oscillator which sequentially activates red and infrared diodes. The duty cycle of the oscillator is regulated by the relative amounts of red and infrared light reflected by the blood. The construction of the sensor allows the sensor to operate with only two conductors, optimizing it for incorporation in a standard, bipolar pacing lead.

1 Claim, 11 Drawing Sheets

OXYGEN SENSING PACEMAKER

CROSS REFERENCE TO COMMONLY ASSIGNED COPENDING APPLICATION

Reference is made to U.S. patent application Ser. No. 896,695 by Baudino et al for an "Oxygen Sensing Pacemaker" filed Aug. 15, 1986.

BACKGROUND OF THE INVENTION

The present invention relates to cardiac pacing generally and in particular to a cardiac pacemaker which regulates pacing rate based upon sensed percentage of oxygen saturation of the blood.

The relationship between oxygen saturation of the blood and pulse rate in a healthy heart is well known. This relationship has given rise to numerous proposals for pacemakers which regulate pacing rate in response to sensed blood oxygen level. These pacemakers attempt to restore the natural relationship between blood oxygen level and pulse rate in order to provide a pacemaker which paces the heart at a rate appropriate to the physiological demands of the patient's body.

An early proposal for such a pacemaker is set forth in U.S. Pat. No. 4,202,339, issued to Wirtzfeld et al. This pacemaker takes the form of an asynchronous pacemaker which does not sense the heart's underlying electrical activity. U.S. Pat. No. 4,467,807, issued to Bornzin and incorporated herein by reference in its entirety discloses a pacemaker in which the oxygen sensor's function is integrated with a sense amplifier for sensing intrinsic heart activity. This approach is believed superior to that of Wirtzfeld in that it avoids competing with underlying heart activity and allows the heart to beat at its own, underlying rhythm if that underlying rhythm is appropriate.

SUMMARY OF THE INVENTION

The present invention provides a refined version of an oxygen sensing pacemaker in which the oxygen sensor is mounted on the pacing lead. The oxygen sensor requires only two conductors for operation, yet includes a two wavelength reflectance oximeter for increased accuracy. Experience in the field of cardiac pacing has shown that one of the more vulnerable portions of the pacing system is the pacing lead, which is exposed to mechanical stresses. Therefore, it is felt that the simpler the structure of the pacing lead is, the more reliable and durable it is likely to be. In addition, reducing the number of conductors to two allows for easier installation of the pacemaker and lead and allows the use of standard bipolar pacemaker and lead connector configurations. For these reasons, an oxygen sensor requiring only two conductors is believed desirable.

The sensor and circuitry are also configured to minimize the current drain imposed by the sensing regime, while retaining the high degree of accuracy and linearity provided by a two wavelength reflectance oximeter. The sensor includes an oscillator which sequentially activates red and infrared diodes. The activation times of the infrared and red diodes are determined by the amounts of infrared and red light reflected by the blood. The sensor draws substantially more current when the red diode is activated than when the infrared diodes are activated. This allows the pacemaker to measure the durations of the red and infrared diode activation periods. This approach provides a signal to the pacemaker which has high resolution, increased noise immunity, and is less affected by long term fluid infiltration into the pacing lead. The intermittent operation provides a desirably low current drain.

DETAILED DESCRIPTION OF THE DRAWINGS

Figure 1:
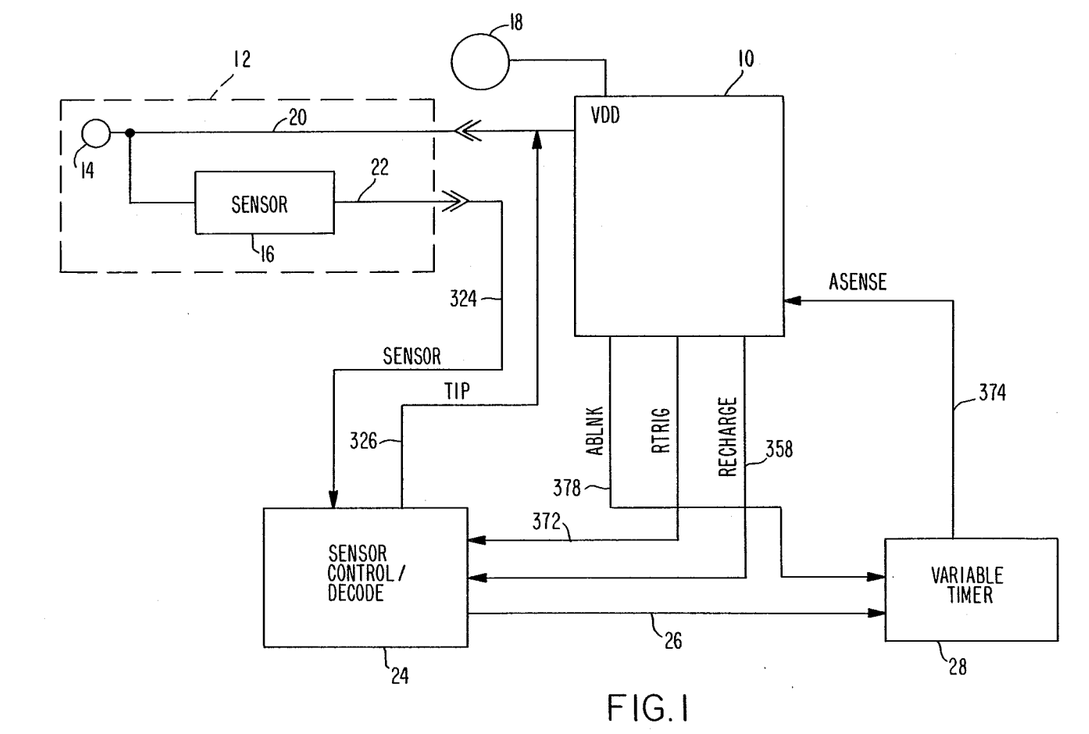
FIG. 1 is a block diagram illustrating the functional relationship of the major elements of the pacemaker.

FIG. 1 is a block diagram of the primary components of the pacemaker. Basic operation of the pacemaker is described in conjunction with the timing diagram in FIG. 2.

The pacemaker is based upon a VDD pacemaker of the type known to the art. Such a pacemaker typically includes a ventricular pacing electrode, an atrial amplifier and a ventricular amplifier, which sense electrical activity in the atrium and ventricle of the heart, respectively. In the present embodiment, the atrial amplifier is dispensed with. However, all timing circuitry associated with the atrial amplifier is retained. In the present embodiment, the VDD pacing circuitry 10 is taken from the Enertrax ® pacemaker, manufactured and sold by the assignee of this application. However, other VDD or DDD pacemakers would provide a suitable starting point, provided they have at least the inputs and outputs discussed below. A more detailed description of such pacemakers can be found in U.S. Pat. No. 3,648,707 issued to Greatbatch and U.S. Pat. No. 4,059,116 issued to Adams, incorporated herein by reference in their entirety.

The basic operation of a VDD pacemaker is well known to those skilled in the art. Typically, in response to a sensed atrial contraction, the circuitry initiates timing of an A-V interval. If no ventricular contraction is sensed during the A-V interval, a ventricular pacing pulse is generated. After a sensed ventricular contraction or a ventricular pacing pulse, if no underlying atrial or ventricular activity occurs within a predetermined V—V interval, a ventricular pacing pulse is generated. In the present invention, the atrial amplifier is dispensed with, and the sensor and associated circuitry provide a signal which the pacing circuitry treats as if it were a sensed atrial contraction. By varying the timing of this simulated atrial contraction, the underlying pacing rate of the pacemaker is controlled.

The pacing circuitry is coupled to the heart by means of a pacing lead 12 which includes a tip electrode 14 and the sensor 16. Pacing occurs between the tip electrode 14 and the can 18 of the pacemaker. Sensing of ventricular activity also occurs between the tip electrode 14 and the can 18 of the pacemaker. The lead 12 has two conductors 20 and 22, coupled to the pacing circuitry 10 and to the sensor control/decode circuitry 24, respectively. Sensor control decode circuitry 24 provides a signal on line 26 indicative of the sensed oxygen saturation percentage.

Figure 2:
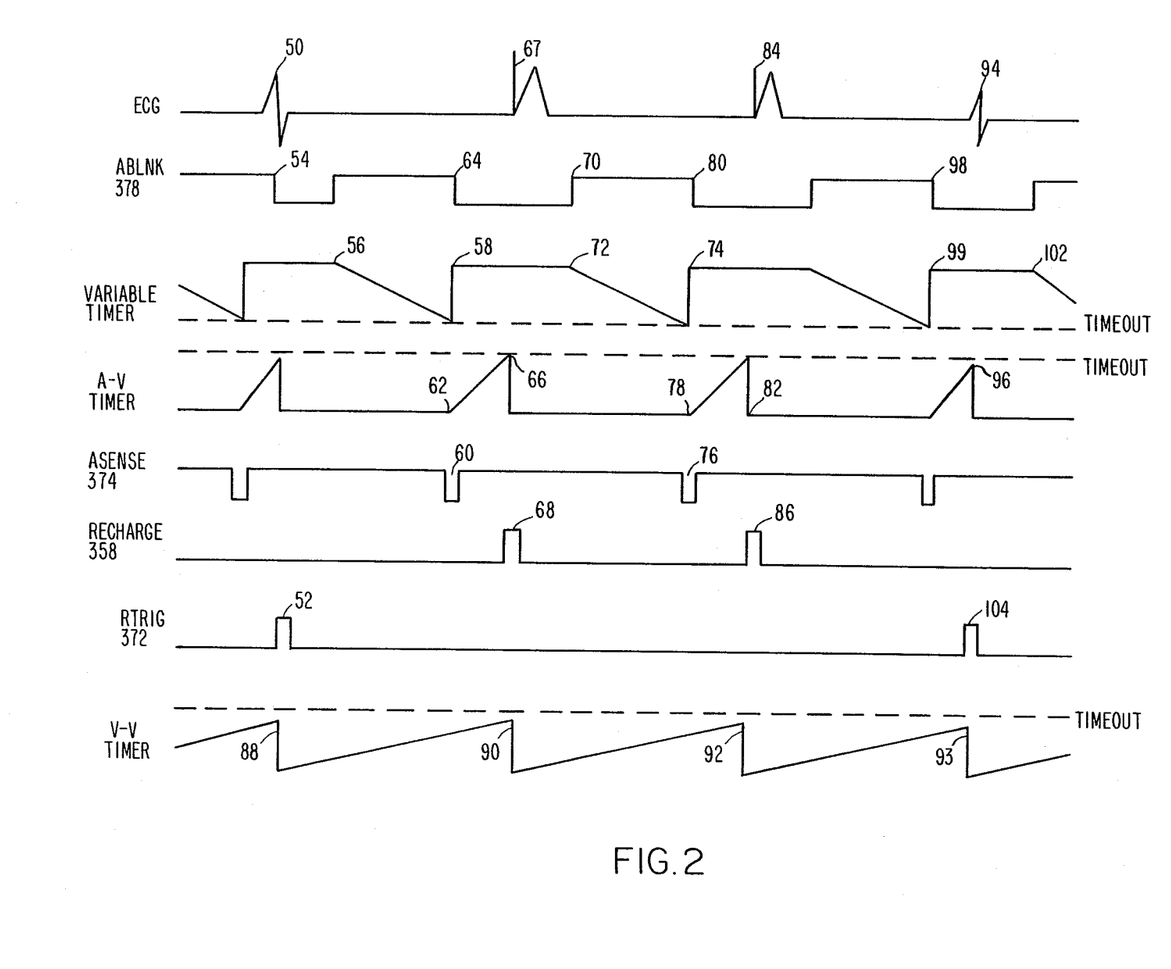
FIG. 2 is a timing diagram illustrating the basic timing of the pacemaker.

The operation of the pacemaker can best be understood in conjunction with the timing diagram in FIG. 2. The ECG trace illustrates the electrocardiogram of a patient in which a pacemaker according to the present invention has been implanted. The first QRS complex 50 is a natural ventricular contraction sensed by the pacing circuitry 10. The sensed contraction causes generation of a pulse 52 on RTRIG line 372. Sensing of the ventricular contraction also initiates an atrial blanking period which prevents the pacer from responding to electrical signals in the atrium. During the atrial blanking period, a low logic signal 54 is generated on ABLNK line 378. The atrial blanking signal extends until 120 ms following the sensed ventricular contraction.

The variable timer 28 (FIG. 1) includes an RC timing circuit controlled by ABLNK line 378 and by the signal indicative of oxygen saturation, provided by the sensor control decode circuitry 24 on line 26. Variable timer 28 begins timing a variable delay interval on expiration of the atrial blanking period at 56. Upon time out of the variable delay interval at 58, timer 28 generates a simulated atrial sense signal 60 on ASENSE line 374.

The simulated atrial sense signal 60 causes the VDD circuitry 10 (FIG. 1) to initiate the timing of the A-V interval at 62. In addition, the simulated atrial sense signal 78 causes the pacing circuitry 10 to initiate the atrial blanking period, driving ABLNK line 378 low at 64. At the expiration of the A-V interval at 66, a ventricular pacing pulse 67 is generated, causing a positive signal 68 on RECHARGE line 358. At the expiration of the atrial blanking interval at 70, timing of the variable delay is reinitiated at 72. Thus, the interval between a sensed contraction 50 and the next subsequent ventricular pacing pulse is determined by the sum of the A-V interval of the plus the variable delay interval determined by variable timer 28 plus 120 ms. The duration of the variable delay interval is determined by the signal on line 26 from the sensor control/decode circuitry 24.

The escape interval following a ventricular paced beat is determined in a similar fashion. Following the pacing pulse 67, the atrial blanking period remains in effect for a period of 120 ms. Upon expiration of the atrial blanking period at 70, variable timer 28 reinitiates timing of the variable delay interval at 72. Time out of the variable delay interval at 74 triggers the generation of simulated atrial sense signal 76 on ASENSE line 374. This in turn initiates timing of the A-V interval at 78, and initiates the atrial blanking period at 80, driving ABLNK line 378 low. At the expiration of the A-V interval at 82, a ventricular pacing pulse 84 is generated followed by a corresponding positive signal 86 on RECHARGE line 358.

Sensed ventricular contraction 94 follows pacing pulse 84 by an interval less than the sum of 120 ms plus the A-V delay plus the variable delay. This terminates timing of the A-V interval at 96. The atrial blanking period initiated at 98 by time out of the variable delay at 99 will terminate at 100, 120 ms following sensed ventricular contraction 94. At that time, timing of the variable delay is reinitiated at 102. A positive going signal on RTRIG line 372 corresponding to sensed beat 94 is illustrated at 104.

Pacing circuitry 10 also includes a V—V timer. As discussed above, this timer sets a minimum pacing rate. This timer is initiated concurrent with either sensed ventricular contractions or ventricular pacing pulses. In the examples of FIG. 2, the V—V timer is initiated at 88, 90 and 92. Because the total of 120 ms plus the A-V delay plus the variable delay was less than the underlying V—V interval, the V—V timer does not time out in FIG. 2. However, in the event that the sum of 120 ms plus the variable delay plus the A-V delay were greater than the V—V interval, pacing would occur on the expiration of the V—V interval.

In summary, the pacemaker operates similarly to the pacemaker disclosed in the Bornzin patent referred to above, in that the escape interval following either a sensed ventricular contraction or a paced ventricular contraction is determined by the sensed oxygen saturation percentage. Like the pacemaker described in the Bornzin patent, sensing of natural ventricular contractions prior to the expiration of the escape interval reinitiates timing of the escape interval.

The signals on RECHARGE line 358 and RTRIG line 372 are provided to the sensor control/decode circuitry 24 where they are counted. After every fourth count, the sensor 16 is activated, and a new value of oxygen saturation is decoded by circuitry 24. This signal indicative of the percentage of saturation is provided to variable timer 28 on line 26, and the variable delay interval is correspondingly changed.

Figure 3:
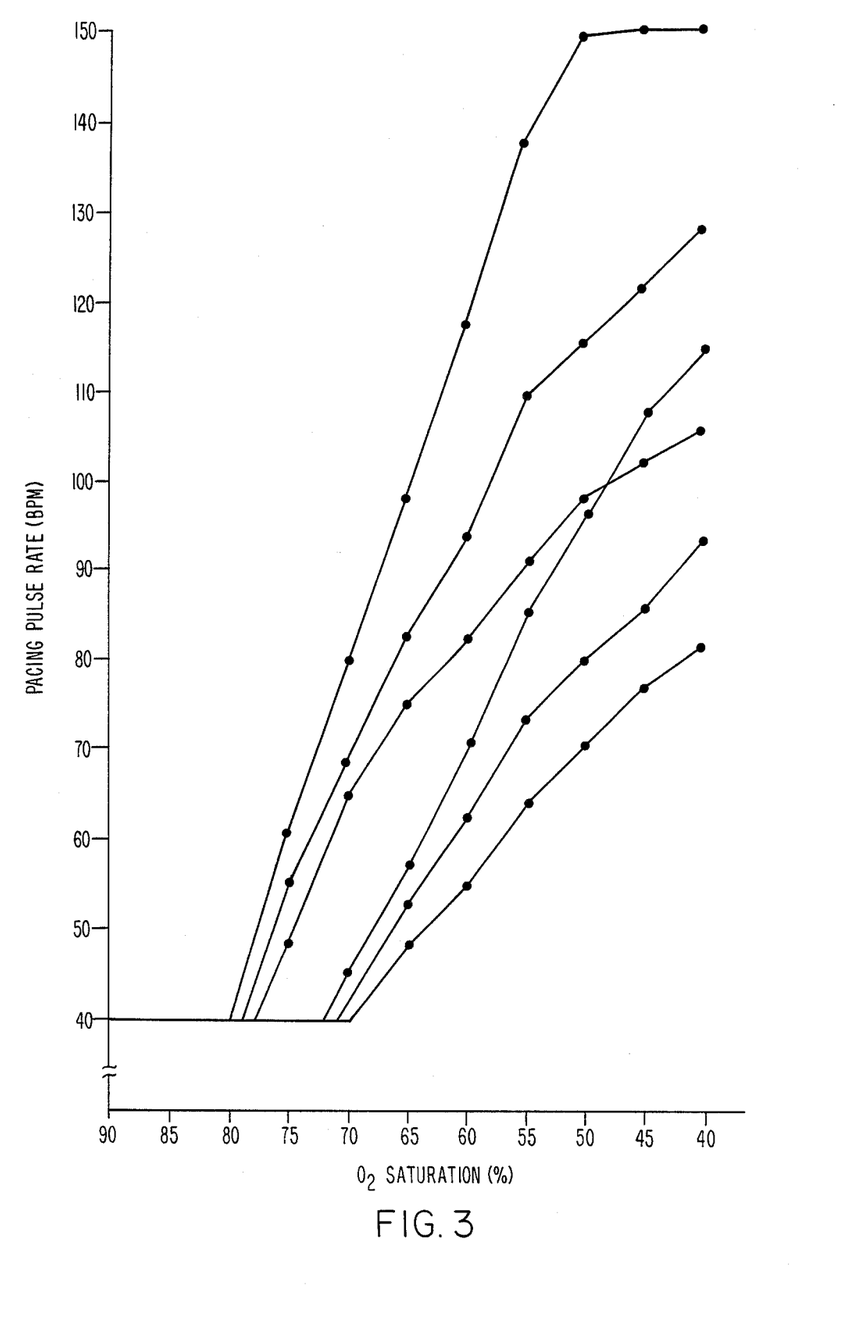
FIG. 3 is a graph illustrating the correlation between the pacing rate provided by the pacemaker and the percentage of oxygen saturation.

FIG. 3 illustrates the various relationships between oxygen saturation and pulse rate available in the pacemaker. The pacemaker provides two sets of curves relating oxygen saturation and pulse rate, which are referred to hereafter as family A and family B. As discussed above, the pacing rate is the sum of the A-V interval, the 120 ms atrial blanking period following ventricular pace or sense, and the variable delay interval determined by the variable timer 28. In the particular VDD pacing circuitry utilized, that of the Enertrax® pacer, there are ten available A-V intervals ranging from 25 ms to 250 ms in 25 ms increments. These control settings determine the curves within family A and family B. For example, the curves illustrated as A10 and B10 employ an A-V interval of 25 ms, while the curves illustrated as A1 and B1 employ an A-V interval of 250 ms.

Figure 10:
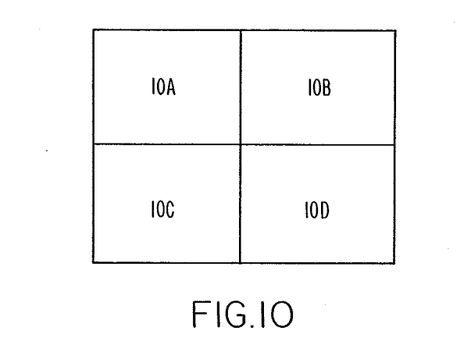
FIG. 10 is a diagram showing how the FIGS. 10A–10D are arranged.

The sensor/control decode logic 24, FIG. 1, provides an output signal on line 26 which is proportional to the sensed oxygen saturation. The specific relationship between sensed oxygen saturation and the output signal on line 26 is adjustable between two settings which define the A and B families of curves illustrated in FIG. 3. At any particular sensed oxygen saturation percentage, the variable delay interval in the B family is about one-half of the corresponding variable delay in the A family. This provides increased flexibility to optimize the pacemaker's operation for the particular patient in which it is implanted. Within each family of curves, any of the 10 A-V intervals may be selected to produce a total of 20 possible response curves. The specifics of the operation of sensor control/decode circuitry 24 and variable timer circuitry 28 are discussed in more detail below in conjunction with the discussion of FIG. 10.

All curves illustrated employ an underlying, V—V interval of 1500 ms, corresponding to 40 beats per minute. This interval is also programmable and determines the lowest available pacing rate. As discussed above, unless the sum of the A-V delay, the variable delay and the 120 ms post ventricular atrial blanking interval is less than the V—V interval, pacing will occur on expiration of the V—V interval.

Figure 4:
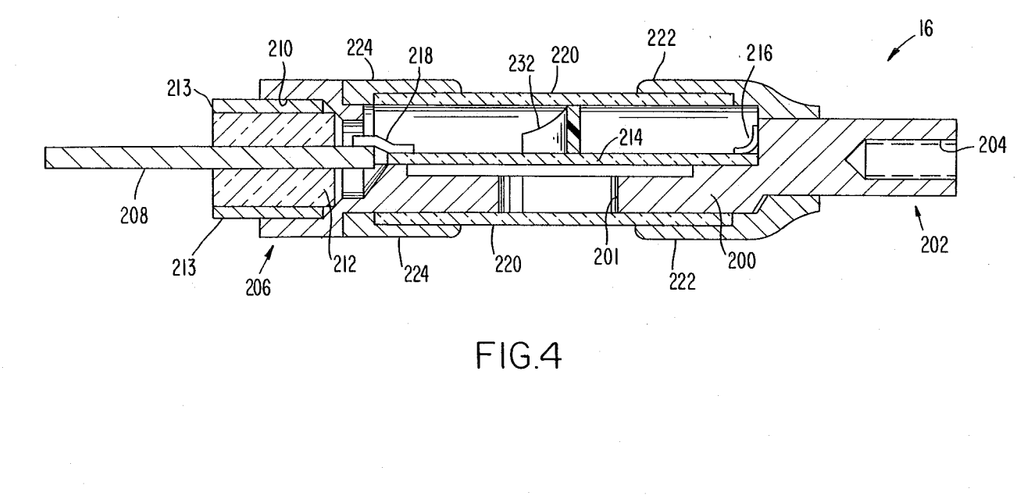
FIG. 4 is a sectional drawing of the assembled oxygen sensor.

FIG. 4 is a sectional drawing of the assembled sensor ready for incorporation in a cardiac pacing lead. The sensor includes a machined sensor body 200 which may be fabricated of titanium. The sensor body 200 serves both as a structural element and as a conductive element. The distal end 202 of sensor body 200 is provided with a bore 204, in which a coiled conductor coupled to the tip electrode 14 (FIG. 1) of the pacing lead 12 (FIG. 1) may be mounted. The proximal end 206 of sensor body 200 is preferably coupled to one of the two elongated conductors 20 and 22 (FIG. 1) in the pacing lead 12. The sensor body 200 thus serves as part of the conductor coupling the pacemaker to the tip electrode. A wire 208 enters the proximal end of the sensor body 200 via bore 210. Bore 210 is sealed by means of feed through 212, which may be fabricated of sapphire and is provided with a metal sheath 213 which is welded to sensor body 200.

Sensor body 200 serves to mount the hybrid circuit 214, which contains the active circuit elements of the sensor and is provided with a central bore 201 to allow access to the bottom of hybrid circuit 214. The circuitry of hybrid circuit 214 is coupled to the sensor body at its distal end by means of strap 216 and is coupled to wire 208 at its proximal end by means of wire 218. Surrounding sensor body 200 is a transparent sapphire tube 220 which allows the infrared and red light generated by the oximeter circuitry on hybrid 214 to exit and to reenter the sensor. Sapphire tube 220 is coupled to sensor body 200 by means of welding collars 222 and 224. Welding collars 222 and 224 are brazed to sapphire tube 220 and welded to sensor body 200. This construction provides a long term, hermetically sealed sensor capsule.

Hybrid circuit 214 includes three LED's, and one photo diode. The three LED's are surrounded by a semicylindrical shield 232 which extends from the surface of hybrid 214 to the inner surface of sapphire tube 220. The photo diode is mounted to the surface of hybrid 214 distal to cylindrical shield 232. This construction minimizes direct propagation of light from the LED's to the photo diode, and thus ensures that almost all light impinging on the photo diode has been reflected off of the patient's blood.

When the sensor is incorporated into a pacing lead, it is expected that a coaxial configuration will be used employing two coiled conductors. The outer conductor will be welded or otherwise attached to the proximal end 206 of sensor body 200 and the inner conductor will be welded or otherwise attached to the proximal end of wire 208. In order to encourage long term operation of the device, the exterior of the sensor capsule may be covered by a transparent, polyurethane sheath, which may be continuous with the outer insulation of the pacing lead and also insulates sensor body 200. This structure is described in more detail in commonly assigned, co-pending application by Baudino et al cited above, and incorporated herein by reference in its entirety.

Figure 5:
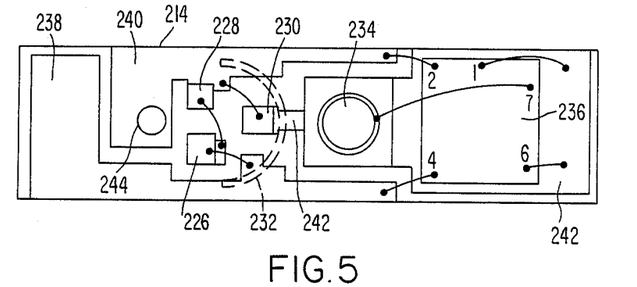
FIG. 5 is a plan view of the top of the hybrid circuit within the sensor.

FIG. 5 shows a top, plan view of hybrid 214. In this view, it can be seen that the hybrid contains two infrared LED's 226 and 228 and one red LED 230. Diodes 226, 228 and 230 are mounted proximal to shield 232. Photo diode 234 is located distal to shield 232. In addition, the hybrid 214 contains an oscillator 236. Oscillator 236 alternately energizes the red diodes 226 and 228 and the red diode 230. The reflected light impinging upon photo diode 234 determines the relative time periods of energization of the infrared diodes 226 and 228 and the red diode 230. During the time when red diode 230 is energized, there is a current flow through the sensor circuitry of approximately 6 ma. While the IR diodes 226 and 228 are energized, there is a current flow through the sensor circuitry of only approximately 2 ma. Due to the intermittent operation of the sensor, the average current drain is only about 10 microamps. The difference in current drain when the red and IR diodes are activated allows the sensor control/decode circuitry within the pacemaker to determine the relative time periods during which the diodes are energized, and thus the ratio of reflected red and infrared light. This mechanism will be discussed in more detail in conjunction with FIG. 10, below. Areas 238, 240 and 242 are metallization areas on the upper portion of the hybrid substrate. Plated through hole 244 couples area 240 to an additional conductive area on the back of the hybrid, as does a second plated through hole located under oscillator 236, coupled to conductive area 242. Wire 218 (FIG. 4) is coupled to area 238. Strap 216 (FIG. 4) is coupled to area 242.

Figure 6:
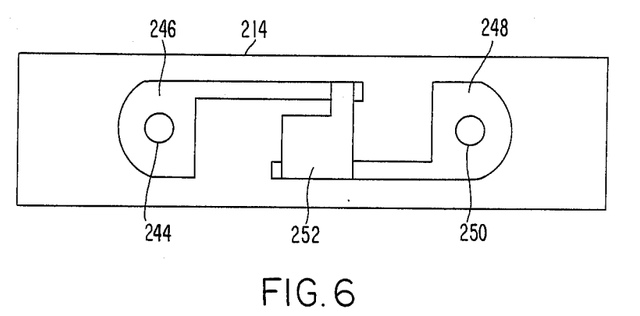
FIG. 6 is a plan view of the bottom of the hybrid circuit within the sensor.

FIG. 6 illustrates the bottom surface of hybrid 214. Conductive areas 246 and 248 are coupled to conductive areas 240 and 242 on the top of hybrid 214 by means of plated through holes 244 and 250, respectively. Resistor 252 is coupled to conductive areas 246 and 248. Resistor 252 is located over bore 201 of sensor body 200 (FIG. 4) when assembled. This allows laser trimming of resistor 252 through the sapphire tube 220. Preferably, resistor 252 is trimmed so that oscillator 236 provides a 50 percent duty cycle for activating the red diode 230 and the infrared diodes 226 and 228 in the presence of blood having an 80 percent oxygen saturation.

Figure 7:
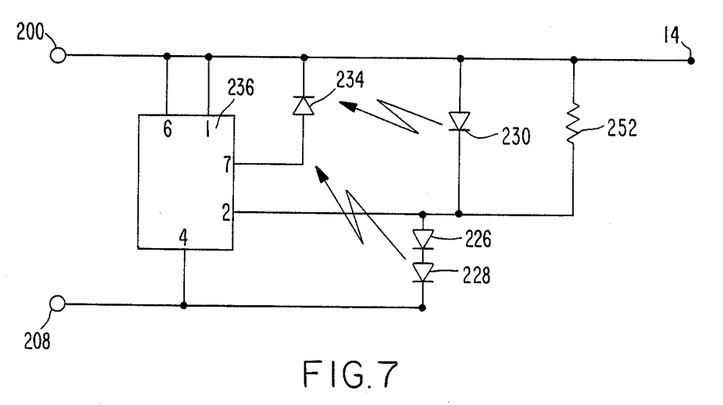
FIG. 7 is a schematic of the hybrid circuit within the sensor.

FIG. 7 is a schematic diagram of the sensor circuitry. In this view, the interrelation of the various circuit components is more clearly visible. The connection of sensor body 200, wire 208 and tip electrode 14 is shown in this drawing. All elements of the drawing correspond to identically labeled elements in FIGS. 4 and 5. When a power signal is provided across wire 208 and sensor body 200, the timing function of oscillator 236 is initiated. Oscillator 236 upon initial turn on activates red diode 230. The timing periods of the oscillator are determined by the parasitic capacitance of photo diode 234, the fixed resistance of resistor 252, and the variable resistance of photo diode 234. The amount of light reflected on photo diode 234 varies its' effective resistance and thus determines the red diode activation period. At the expiration of the red diode activation period, oscillator 236 activates diodes 226 and 228. The infrared light reflected upon photo diode 234 thereafter determines the length of the IR diode activation period. At the expiration of the IR diode activation period, the red diode is again activated. This oscillation continues until the power signal is removed from wire 208 and sensor body 200. There is a four-fold change in the ratio of infrared to red diode activation intervals between resting and heavy exercise. The modulation of the power signal to sensor 16 thus allows oxygen saturation percentage to be determined with a high degree of resolution.

Figure 8:
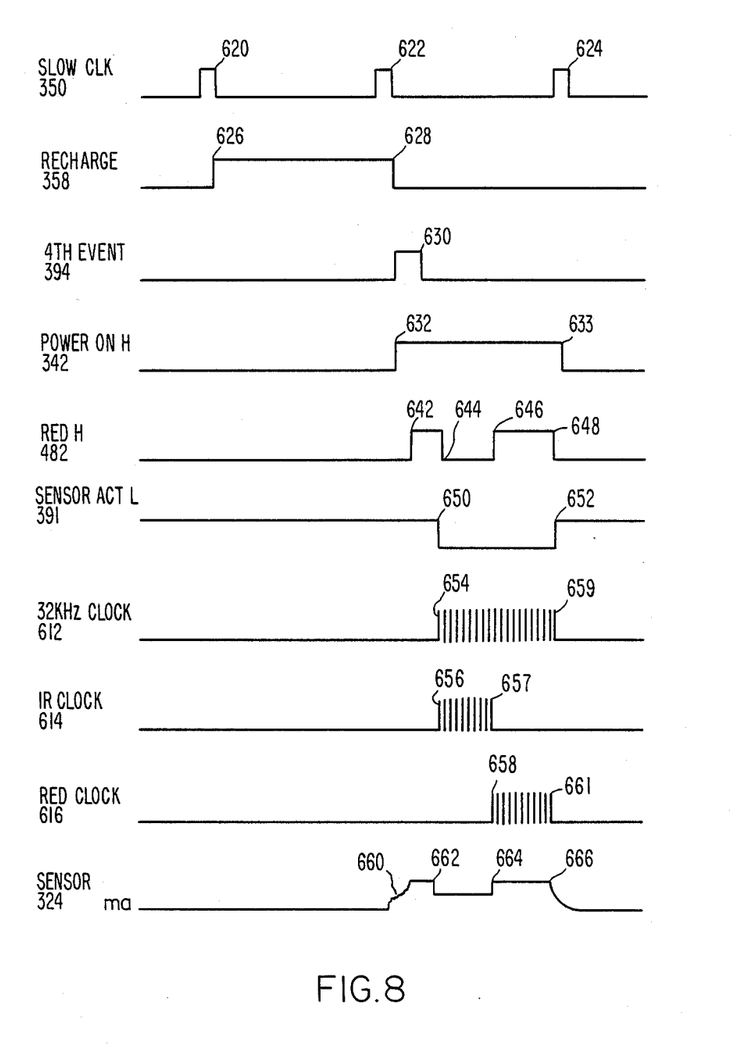
FIG. 8 is a timing diagram illustrating the operation of the sensor and associated circuitry.
Figure 9:
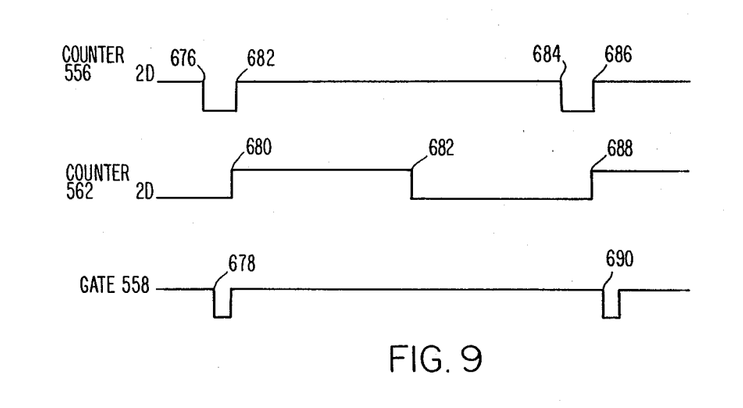
FIG. 9 is a timing diagram illustrating the operation of circuitry which decodes the signals provided by the sensor to provide a signal indicative of oxygen saturation.

FIGS. 8 and 9 are timing diagrams which illustrate the operation of the sensor and associated circuitry. These timing diagrams are discussed in conjunction with the schematics of the circuitry in FIG. 10, and should be referred to in conjunction with FIG. 10 in order to understand the operation of the pacer more fully.

Figure 10A:
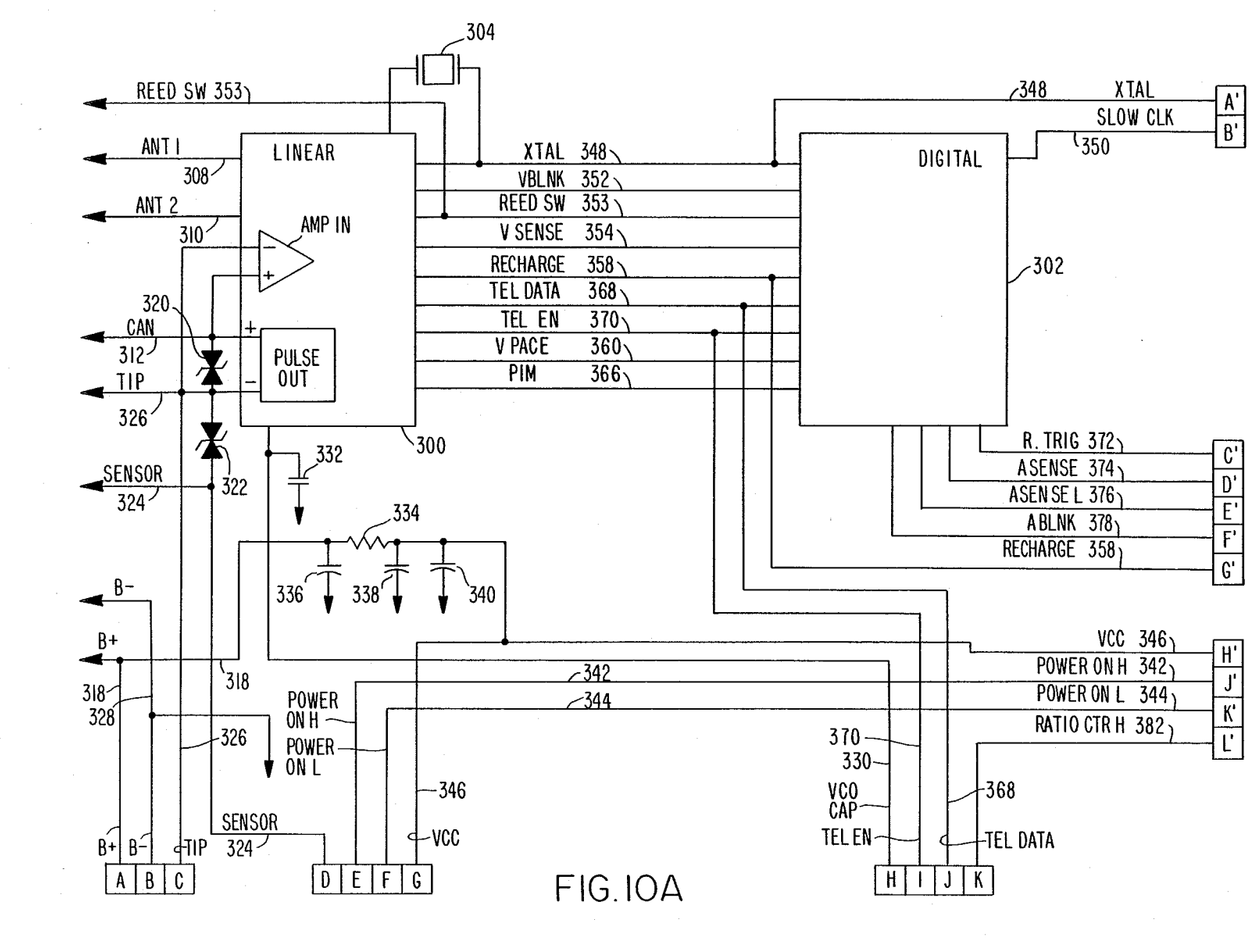
FIGS. 10A–10D show a schematic of the pacemaker.

FIGS. 10A, B, C and D illustrate the circuitry associated with the sensor and its interconnection to a prior art VDD pacemaker circuitry. In particular, the prior art VDD pacemaker circuitry includes linear and digital circuitry of the Enertrax ® pacemaker, previously marketed by Medtronic, Inc., with the exception of the atrial sense amplifier, which is omitted. While this circuitry is shown as exemplary, the sensor and associated circuitry are believed to be easily adapted to any modern programmable VDD or DDD pacemaker circuitry which will provide the required inputs, outputs and timing periods.

Linear circuitry 300 contains the ventricular sense amplifier, the ventricular output amplifier, and circuitry associated with telemetry into and out of the pacemaker. Linear circuitry 300 is coupled to the antenna via ANT 1 line 308 and ANT 2 line 310. Both the input amplifier and the output amplifier of linear circuitry 300 are coupled to the tip electrode 14 and to the pacemaker can 18 via lines 312 and 26. Zener diodes 320 provide protection for the sense amplifier in the event of electrocautery or defibrillation. SENSOR line 324 is coupled to TIP line 326 by means of back to back zener diodes 322, also protecting the pacing circuitry in the event of applied defibrillation or electrocautery. TIP line 326 and SENSOR line 324 in use are coupled to conductors 20 and 22 (FIG. 1) of the pacing lead 12 (FIG. 1). Timing for the pacemaker is based upon a 32 KHz crystal oscillator 304 which is coupled to both the linear and to the digital circuitry.

Digital circuitry 302 takes care of the timing functions of the pacemaker, including timing of the A-V interval, the V—V interval and the atrial blanking period discussed in conjunction with FIGS. 1 and 2, above. Digital circuit 302 also times out a ventricular refractory period, as is conventional in VDD pacers. In the Enertrax ® pacer circuitry, this is a programmable parameter. Digital circuit 302 also times out a ventricular blanking period, as is conventional. Expiration of the ventricular blanking period is indicated by a signal on VBLNK line 352. On expiration of the V—V or A-V intervals, digital circuitry 302 generates a signal on VPACE line 360 and a subsequent recharge signal on RECHARGE line 356. In response to a sensed ventricular contraction, linear circuitry 300 generates a signal on VSENSE line 354 which in turn triggers generation of a signal on RTRIG line 372. PIM line 366 carries data received by the linear circuitry 300 to digital circuitry 302 to select programmable time intervals, including the A-V interval and the V—V interval and to select other programmable options such as atrial amplifier sensitivity.

ASENSE line 374 is the input to the digital circuit 302 which would normally receive the output of the atrial sense amplifier. ASENSEL line 376 is an output from digital circuitry 302, and indicates the atrial sensitivity level selected via programming. As there is no atrial amplifier, this line is used to select between the A and B families of curves and to disable the sensing function. ABLNK line 378 is an output from digital circuitry 302 and is low during the atrial blanking interval.

In addition, digital circuitry 302 provides outputs controlling the operation of the telemetry functions of the linear circuitry 300. These include a telemetry enable signal, generated on TELEN line 370 and a telemetry data signal generated on TELDATA line 368. The TELEN line 370 is high when telemetry function is enabled, which occurs only in the presence of a low signal on REEDSW line 353. TELDATA line 368 is high when the device is telemetering out digital information from the memory of digital circuitry 302. When TELEN line 370 is high and TELDATA line 368 is low, the device is adapted for analog telemetry. Normally, the pacemaker would telemeter out the electrocardiogram sensed by the tip electrode 14. Telemetry of this information takes the form of pulse interval modulation, based upon the current applied to VCO capacitor 332. In the present invention, the current applied to VCO capacitor 332 is used to telemeter out the sensed oxygen saturation.

The programming and timing functions of prior art VDD pacemakers are discussed in more detail in U.S. Pat. No. 4,344,437 issued to Markowitz, incorporated herein by reference in its entirety. It is believed that one skilled in the art would be familiar with these basic functions, which would be present in most modern VDD and DDD pacemakers, and that the basic sensor related circuit architectures set forth herein would be easily adaptable to such pacemakers.

The positive terminal of the battery is coupled to B+ line 318, which is coupled to capacitors 336, 338 and 340 along with resistor 334 to provide the VCC signal on VCC line 346. This is used as the basic power signal for the sensor control and timing circuitry. The negative terminal of the battery is coupled to B— line 328 and to ground. The pacemaker is preferably powered by an LiMnO$_2$ cell, which generates a three volt output and has low internal impedance. The low impedance of the cell allows it to abruptly increase its current output when required by sensor activation. Basic timing functions for the sensor circuitry are taken from the 32 KHz crystal oscillator via XTAL line 348 and from the pacemaker slow clock via SLOWCLK line 350. SLOWCLK line 350 merely provides a clock signal at 8 ms intervals. FIG. 10A also illustrates interconnect lines including the POWERON H line 342, POWERON L line 344, and RATIOCTR H line 382.

Figure 10B:
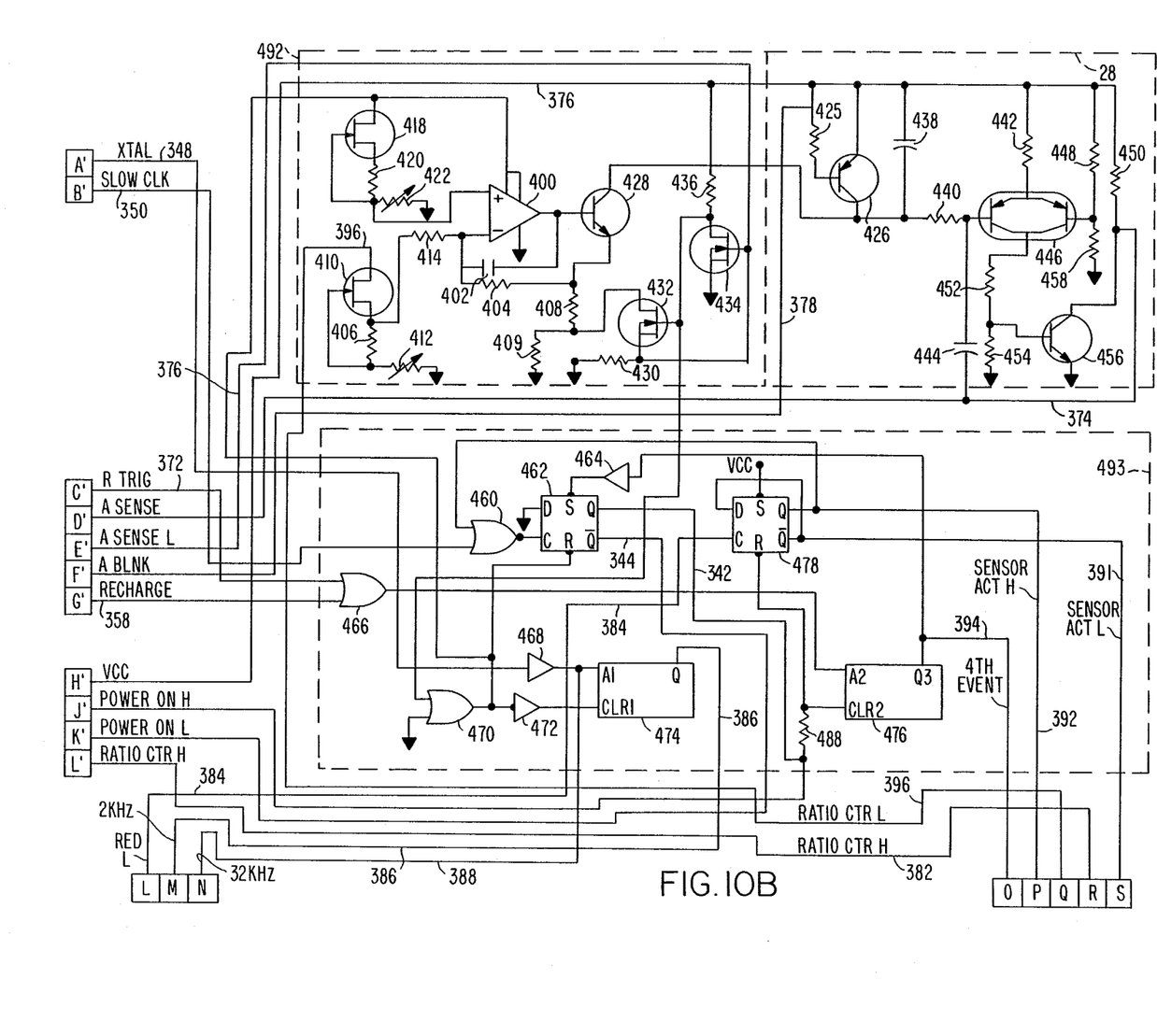

FIG. 10B includes the variable timer 28, illustrated in FIG. 1, along with a portion of the sensor control and decoding circuitry 24. For purposes of convenience, the sensor control and decode circuitry on FIG. 10B can be divided into square wave to DC circuit 492 and sensor control circuitry 493.

Sensor control circuitry 493 uses the outputs of digital circuitry 302 to control sensor timing and operation. Pacing and sensing events are counted by counter 476, which is incremented by OR gate 466 which is responsive to either a signal on the RECHARGE line 358 or on RTRIG line 372. As such, with each sensed ventricular contraction or ventricular pacing pulse, counter 476 is incremented by 1. When the counter reaches a count of four, 4TH EVENT line 394 goes high. This initiates sensor operation. In addition, when the fourth event is counted, a negative set signal is applied to flip-flop 462 via inverter 464. This causes a high signal on the Q output of flip-flop 462. This in turn serves as a clear signal for counter 476 through resistor 488. The clear signal sets the output of Q3 of counter 476 low, driving the signal on 4TH EVENT line 394 low and removing the negative set signal from flip-flop 462. When flip-flop 462 is set, POWERON H line 342 goes high. The $\overline{Q}$ output of flip-flop 462 correspondingly sets POWERON L line 344 low.

When POWERON H line 342 goes high, the negative reset is removed from flip-flop 478. Flip-flop 478 keeps track of the operation of the sensor, and enables the sensor to operate for one full infrared and one full red time period. When the signal on RED L line 384 goes high, indicative of the beginning of the first infrared diode activation interval, the Q output of flip-flop 478 goes high generating a high signal on SENSORACT H line 392. On the beginning of the next infrared activation period, the signal on RED L line 384 will go high again, clocking the $\overline{Q}$ output of flip-flop 478 through, setting SENSORACT H line 392 low. The $\overline{Q}$ output of flip-flop 478 controls the logic level of SENSORACT L line 391.

FIG. 10B also includes circuitry which disables the sensor in the event that the programming of the device indicates that sensor operation is not desired. In the event that sensor operation is not desired, ASENSEL line 376 is set high, which causes FET 434 in the square wave to DC circuit 492 to generate a low signal on the input of OR gate 478. OR gate 478 in turn generates a negative reset signal to flip-flop 462, preventing the POWERON H line 342 from going positive to provide power to the sensor.

Counter 474 functions to divide the 32 KHz signal on XTAL line 348 by 16. This provides a 2 KHz square wave signal on 2 KHz line 368. When the sensor is disabled, the negative signal from OR gate 478 is invented by inverter 472 to provide a positive clear signal to counter 474, preventing its operation. Inverter 468 inverts the signal on XTAL line 348. This inverted signal appears on 32 KHz line 388, where it is subsequently used by the sensor decoding circuitry illustrated in FIG. 10D.

Figure 10C:
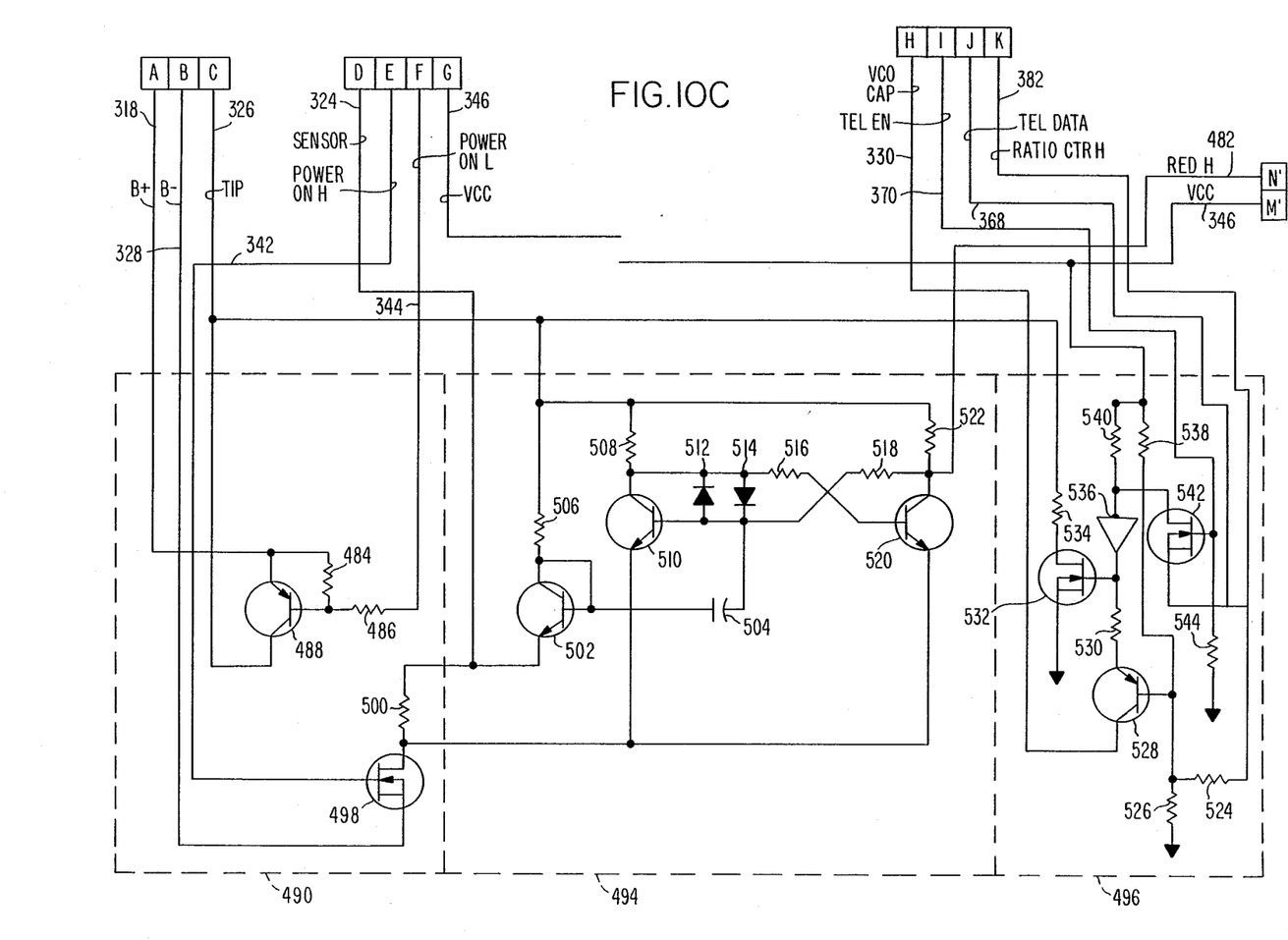

FIG. 10C includes several circuit blocks. Circuit block 490 is the sensor bias circuitry which powers the sensor 16 (FIG. 1). In response to a low signal on POWERON L line 344, transistor 488 and associated resistors 484 and 486 couple B+ line 318 to TIP line 326, which is coupled to sensor body 200 (FIG. 4). The high logic signal on POWERON H line 342 turns on FET 498 and provides a return path to ground (B−) for SENSOR line 324.

To understand the operation of this circuit, reference is made to the timing diagram of FIG. 8. RECHARGE line 358 goes high at 626 concurrent with the negative edge of the slow clock at 620. It remains high until the expiration of the next subsequent slow clock pulse 622. The negative going edge 628 of the recharge pulse clocks counter 478 (FIG. 10B). Assuming it is the fourth count, counter 476 drives 4TH EVENT line 394 high at 630. As discussed above, this sets the Q output of flip-flop 462 (FIG. 10B) high at 632. This turns on transistors 488 and 498 and provides power to the sensor circuitry. When transistors 488 and 498 are turned on, oscillator 236 (FIG. 7) is activated, causing current to flow through red diode 230 (FIG. 7). However, start up transients make the current level 660 on SENSOR line 324 initially unstable. This first red diode activation period is therefore not appropriate for use, and is ignored.

When the initial signal on SENSOR line 324 reaches approximately 4 ma due to red LED 230 activation, the circuitry in circuit block 494 is activated. Transistors 510 and 520, and associated resistors 508, 516, 518 and 522, along with diodes 512 and 514 act as a toggle flip-flop with a predetermined power-up state in which transistor 510 is off and transistor 520 is on. Diodes 512 and 514 are collector clamp diodes for transistor 510, and limit the collector voltage swing to 1.2 volts. This enhances the switching time of transistor 510 and reduces the current drain. When the current on SENSOR line 324 exceeds 4 ma, the flip-flop including transistors 510 and 520 is triggered via trigger capacitor 504, resistor 506 and transistor 502. This turns transistor 520 off, driving RED H line 482 high at 642 (FIG. 8).

Figure 10D:
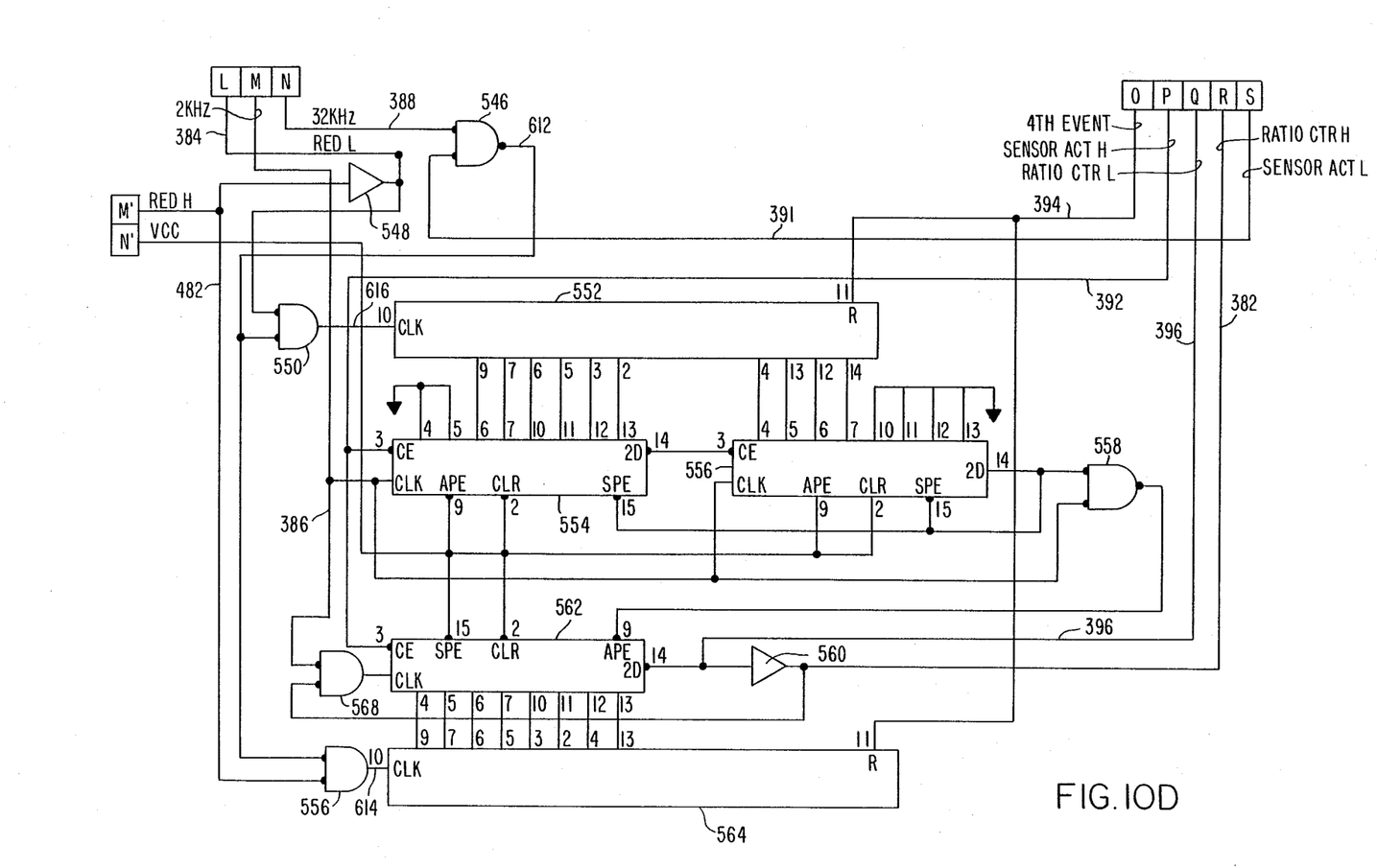

At the expiration of the first red LED activation interval at 662, the signal on SENSOR line 324 drops to 2 ma with the activation of the two IR diodes 226 and 228 (FIG. 7). This again toggles the flip-flop, turning transistor 520 on and 510 off. This sets the signal on RED H line 482 low at 644 (FIG. 8). The low signal on RED H line 482 is inverted via inverter 548 (FIG. 10B) and provided as a high signal on RED L line 384 (FIG. 10D). This signal acts as clock to flip-flop 478 (FIG. 10B), setting SENSORACT H line 392 high at 650 (FIG. 8).

To follow the operation of the decoding circuitry further, it is necessary to refer to FIG. 10D. FIG. 10D should also be reviewed in conjunction with the timing diagrams of FIGS. 8 and 9.

FIG. 10D illustrates the counter system used for decoding the ratio of the IR diode activation period to the red diode activation period. Counters 552 and 564 count the red and infrared diode activation periods, respectively. The high signal 630 (FIG. 8) on 4TH EVENT line 394 resets counters 552 and 564. SENSORACT L line 391 goes low at 650 (FIG. 8). This allows the 32 KHz signal on line 388 to pass through negative input NAND gate 546 on line 612 at 654 (FIG. 8). Simultaneously, SENSORACT H line 392 goes high, disabling counters 562, 554 and 556. Because RED H line 482 is then low at 644 (FIG. 8), negative input NAND gate 556 is enabled to pass through the 32 KHz signal on line 614 at 656 (FIG. 8). This serves as the clock signal to drive IR counter 564. The 32 KHz signal is applied to the clock input of counter 564 until the oscillator 236 (FIG. 7) activates the red diode. When the diode 230 is activated at 664, RED H line 482 is set high at 646 (FIG. 8). When RED H line 482 goes high, this in turn prevents the 32 KHz signal from passing through negative input AND gate 556 to line 614, as illustrated at 657 (FIG. 8). Negative input AND gate 550 is then enabled to pass the 32 KHz signal through on line 616 at 658 (FIG. 8) to serve as a clock signal to counter 552. At the expiration of the red LED activation period at 666, RED H line 482 goes low at 648.

When RED H line 482 goes low, the signal is passed through inverter 548 to RED L line 384, which in turn clocks flip-flop 478 (FIG. 10B), driving SENSORACT L line 391 high and SENSORACT H line 392 low at 650 (FIG. 8). The Q output of flip-flop 478 also clocks flip-flop 462 (FIG. 10B) via NOR gate 460, to drive POWERON H line 342 low and POWERON L line 344 high at 633 (FIG. 8), turning off transistors 488 and 498 (FIG. 10C) and turning off the sensor.

When the signal on SENSORACT H line 392 goes low, this provides a negative counter enable signal to counters 554 and 556, which function as jam in down counters, taking inputs from red counter 552. A low signal on SENSORACT H line 392 also enables counter 562 which acts as a jam in down counter for counting down the number stored in counter 564. Counters 554, 556 and 562 receive clock signals from the 2 KHz line 386 and resume counting. The contents of counters 552 and 564 will be jammed in timing cycles thereafter until the sensor is reactivated.

Counters 554, 556 and 562 all are clocked by the 2 KHz signal on line 386. Because the contents of counter 552 are jammed into counters 554 and 556 beginning with the third counter stage while the contents of counter 564 are jammed into counter 562 beginning with the first counter stage, time out of counter 556 is always later than time out of counter 562. When counter 562 counts down to 0, the 2 KHz clock signal to counter 562 is disabled via inverter 560 and negative input AND gate 568. This also sets the signal on RATIOCTR L line 396 low and the signal on RATIOCTR H line 382 high. Counter 562 remains disabled until counter 556 counts down to 0. When counter 556 counts down to 0, the contents of counter 552 are again jammed into counters 554 and 556 and on the next subsequent 2 KHz clock cycle, the contents of 564 are jammed into counter 562 via negative input NAND gate 558. This also sets RATIOCTR L line 396 low and RATIOCTR H line 382 high. RATIOCTR L line 396 thus provides a modulated square wave signal in which the duty cycle is based upon the relative time outs of counters 556 and 552.

Basic timing of the circuitry of FIG. 10D is illustrated in FIG. 9, which shows counter 556 reaching 0, driving its zero detect output low at 676. On the next subsequent negative going transition of the 2 KHz signal on line 386, the output of negative input NAND gate 558 goes low at 678. This causes the contents of counter 564 to be jammed into counter 562 at the next positive going transition of the 2 KHz signal on line 386, at 680. On that same positive going transition, the contents of counter 552 are jammed into counter 554, causing the zero detect output of counter 556 to go high at 682. Counters 562, 554 and 556 continue to count until the zero detect output of counter 562 goes low at 682. This negative signal is inverted by inverter 560 and applied to negative AND gate 568 to disable further counting by counter 562. In the meantime, counter 556 continues to count until its zero detect output goes low at 684, initiating the restart of counters 554 and 556 at 686 and the restart of counter 562 at 688, as a result of the signal at 690 from NAND gate 558. RATIOCTR L line 396 is taken from the zero detect output of counter 564.

Further decoding of the sensor value takes place in the circuitry in FIG. 10B, which should be examined in conjunction with the timing diagram of FIG. 8. The signal on RATIOCTR L line 396 is applied to the square wave to DC circuit 492. This circuitry converts the square wave signal on RATIOCTR L line 396 to a DC current, proportional to the duty cycle of the square wave signal. The signal on RATIOCTR L line 396 is applied to J-FET 410, which, in conjunction with associated resistors 406 and 412, clamp the high level voltage of the square wave signal from RATIOCTR L line 396 at approximately 2.5 volts. This signal is applied to the negative input of differential amplifier 400 via resistor 414. J FET 418, in conjunction with associated resistors 420 and 422 provides an offset reference voltage of approximately 0.5 volts DC which is provided to the positive input of differential amplifier 400. Differential amplifier 400 in conjunction with FET's 432, 434 and associated resistors 436, 430, 408, 404 and capacitor 402 provide a controlled current sink through transistor 428.

FETs 432 and 434 are controlled by the signal level on ASENSEL line 376. When the signal on ASENSEL line 376 is high, FET 434 is on and sensor operation is disabled via OR gate 470, as discussed above. When the signal on ASENSEL line 376 is low, transistor 432 is activated. This provides greater currents through transistor 428, resulting in a shorter range of variable delay intervals generated by variable timer 28. This setting of ASENSEL produces the B family of curves, described above in conjunction with FIG. 3. If the signal on ASENSEL line 376 is merely a high impedance state, then FET 432 is off. This reduces current flow through transistor 428 and produces the A family of curves, described above in conjunction with FIG. 3.

In summary, the function of the square wave to DC current circuit 492 is to provide a current sink proportional to the duty cycle of the signal on RATIOCTR L line 396. The logic state of ASENSEL line 376 allows the choice of two relationships between the duty cycle on RATIOCTR L line 396 and the current sink provided through transistor 428.

The variable timer circuitry 28 includes a timing capacitor 438, with a charging rate proportional to the current through transistor 428. When the voltage on capacitor 438 reaches a predetermined threshold voltage, it is detected by the threshold detector circuitry including transistors 446, 456 and associated resistors 440, 452, 454, 458, 448 and 450 and capacitor 444. When the voltage on capacitor 438 reaches the threshold voltage determined by resistors 448 and 458, voltage detector transistors 446 turn on transistor 456, driving ASENSE line 374 low. This is the simulated atrial sense signal which is used to initiate timing of the A-V interval by digital circuit 302 (FIG. 10A), as discussed above in conjunction with FIGS. 1, 2 and 3. The low signal on ASENSE line 374 initiates the atrial blanking period, driving ABLNK line 378 low, turning on transistor 426 which discharges capacitor 438 and disables variable interval timer 28. At the expiration of the atrial blanking period, ABLNK line 378 will go high, restarting variable timer 28.

FIG. 10C includes ratio square wave telemetry circuit 496, which allows for telemetry of the measured oxygen value out of the pacemaker to an external programmer. In the Enertrax ® pacemaker, telemetry of analog information is accomplished by varying the charging current to VCO capacitor 332 (FIG. 1) to modulate the pulse intervals of telemetry signals provided to the antenna by linear circuitry 300. This system is generally described in U.S. Pat. No. 4,556,063 issued to Thompson et al, and U.S. Pat. No. 4,374,382 issued to Markowitz, incorporated herein by reference in their entirety.

Transistor 528 serves as an external current source to modulate the voltage on VCO capacitor 332. The square wave signal on RATIOCTR H line 382 is divided by resistors 524 and 526 and applied to the base of transistor 528. Transistor 528 is controlled by FET 542, which turns on transistor 528 via inverter 536 and resistor 530 only when the signal on TELEMEN line 370 is high and when the signal on TELEMDATA line 368 is low. This indicates that the pacing circuitry is enabled for telemetry transmission and that no digital telemetry is being transmitted at that time. In addition, FET 542 also activates FET 532 which prevents electrical signals in the heart from affecting the VCO capacitor 332. In the event that the sensor circuitry is activated during telemetry, it will still function normally, due to the high impedance of resistor 534, which allows TIP line 326 to go high when transistor 488 is turned on. The high impedance of resistor 326 also allows generation of pacing pulses during telemetry of the sensed oxygen saturation percentage.

| COMPONENT LISTING | | | |
|---|---|---|---|
| Counters | Type | Transistors | Type |
| 554,556,562 | HC40103 | 432,434,532,542 | 3N169 |
| 552,564 | HC4040 | 410,418 | 2N4338 |
| 474,476 | HC393 | 498 | VN35 |
| Flip-Flops | | 488 | 2N2907 |
| 462,478 | HC74 | 502,510,520 | 2N2484 |
| OR-Gates | | 456,428 | 2N2484 |
| 466,470 | HC32 | 528,426 | 2N3799 |
| NOR-Gates | | 446 | 2N3811 |
| 460 | HC02 | Amplifier | |
| NEG. AND Gates | | 400 | TLC251 |
| 550,556,568 | HC02 | Oscillator | |
| NEG. NAND Gates | | 236 | ICM7242 |
| 546,558 | HC32 | Diodes | |
| Inverters | | 512,514 | 1N914 |
| 536,548,560 | 4069 | 226,228 | OPC-123 TRW |
| 468,472,464 | 4069 | | |
| Capacitors | Value | 234 | OPC-910 TRW |
| 402 | 2.2 uF | | |
| 336 | 100 uF | 230 | H-1000 Stanley |
| 338 | 68 uF | | |
| 340 | .01 uF | Resistors | Value |
| 444 | 560 pF | 334 | 5K Ohms |
| 504 | 1 uF | 484 | 18K Ohms |
| 332 | 150 pF | 486,508,506 | 10K Ohms |
| 438 | .68 uF | 516,522 | 10K Ohms |
| | | 454,534,540 | 1 M Ohms |
| | | 538,436,450 | 1 M Ohms |
| | | 480,452 | 1 M Ohms |
| | | 530,524 | 15 M Ohms |
| | | 544,430 | 10 M Ohms |
| | | 526 | 5 M Ohms |
| | | 422 | 150K–350K Ohms |
| | | 412 | 250K–1.5 M Ohms |
| | | 420,406 | 226K Ohms |
| | | 414 | 3.3 M Ohms |
| | | 404 | 5.5 M Ohms |
| | | 408,409 | 374K Ohms |
| | | 425 | 3 M Ohms |
| | | 440 | 750K Ohms |
| | | 442 | 560K Ohms |
| | | 448 | 600K Ohms |
| | | 458 | 2.2 M Ohms |
| | | 500 | 10 Ohms |
| | | 252 | 400 Ohms |

-continued

| COMPONENT LISTING | |
|---|---|
| 518 | 470K Ohms |

The above description sets forth the invention in its present form. However, the invention should not be considered as limited to the specific sensor and associated circuitry disclosed herein. In the particular embodiment disclosed herein, the sensor and associated circuitry are optimized for use in conjunction with the circuitry from a particular prior art pacer. However, the invention should not be considered limited to such an embodiment.

In conjunction with the above description, we claim:

1. A cardiac pacemaker of the type comprising pulse generating means for generating cardiac pacing pulses, timing means coupled to said pulse generator means for causing said pulse generator means to generate said pacing pulses at controlled intervals, and a cardiac pacing electrode coupled to said pulse generator for applying said pacing pulses to the heart, wherein said pacemaker further comprises sensor means for sensing the percentage of oxygen saturation of the blood, said sensor comprising:

red light source means for generating red light;
infrared light source means for generating infrared light;
oscillator means for sequentially activating said infrared light source means for an infrared activation period and for activating said red light source means for a red activation period;
means for allowing said red and infrared light generated by said red and infrared light sources to exit said sensor and impinge upon the blood and to allow said red and infrared light reflected by said blood to reenter said sensor;
light sensing means for sensing said red and infrared light reentering said sensor body and for regulating said red activation period and said infrared activation period dependent upon the amount of said red and infrared light reflected by the blood; and
means for applying a power signal to said sensor; and
wherein said sensor means modulates said power signal applied to said sensor means in accordance with said red activation period and said infrared activation period; and
wherein said pacemaker further includes monitor means for monitoring said modulated power signal applied to said sensor and for determining the relative durations of said red and infrared periods and a timing adjustment means coupled to said monitor means for adjusting the time interval of said pacing pulses generated by said pacemaker in accordance with the relative durations of said red and infrared periods.

* * * * *